United States Patent
Sakuma

(10) Patent No.: US 6,217,505 B1
(45) Date of Patent: *Apr. 17, 2001

(54) MEDICAL FABRIC GOODS

(75) Inventor: Tetsuo Sakuma, Suita (JP)

(73) Assignee: Shinfuji Kogyo Kabushiki Kaisha, Osaka (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/914,756

(22) Filed: Aug. 20, 1997

Related U.S. Application Data

(63) Continuation of application No. 08/605,786, filed on Feb. 22, 1996, now abandoned.

(30) Foreign Application Priority Data

| Feb. 23, 1995 | (JP) | 7-034981 |
| Apr. 3, 1995 | (JP) | 7-77559 |
| Jun. 13, 1995 | (JP) | 7-146161 |
| Jun. 30, 1995 | (JP) | 7-165273 |

(51) Int. Cl.⁷ ................................................ A61N 1/00
(52) U.S. Cl. ................................................ 600/15
(58) Field of Search ........................ 600/9, 10, 13–15

(56) References Cited

U.S. PATENT DOCUMENTS

| 4,330,892 | * | 5/1982 | Fukushima | 600/15 |
| 4,480,596 | * | 11/1984 | Shumiyashu | 600/15 |
| 4,548,208 | * | 10/1985 | Niemi | 600/14 |
| 4,587,956 | * | 5/1986 | Griffin et al. | 600/15 |
| 4,641,633 | * | 2/1987 | Delgado | 600/13 |
| 5,131,904 | * | 7/1992 | Markoll | 600/14 |
| 5,226,185 | * | 7/1993 | Guay et al. | 600/15 |
| 5,468,529 | * | 11/1995 | Kwon et al. | 428/36.1 |
| 5,707,333 | * | 1/1998 | Bakst | 600/15 |
| 5,720,046 | * | 2/1998 | Lopez et al. | 600/15 |
| 5,782,743 | * | 7/1998 | Russell | 600/15 |
| 5,807,233 | * | 9/1998 | Sakuma et al. | 600/15 |
| 5,882,292 | * | 3/1999 | Miyaguchi | 600/15 |
| 5,908,444 | * | 6/1999 | Azure | 600/14 |

FOREIGN PATENT DOCUMENTS

| 88 01 358 U | 6/1988 | (DE) . | |
| 0 100 050 A2 | 2/1984 | (EP) . | |
| 0 425 467 A2 | 5/1991 | (EP) . | |
| 2 152 379 | 8/1985 | (GB) . | |
| 0 141 865 | 5/1985 | (JP) . | |
| 61-1525 | 1/1986 | (JP) . | |
| 5-70553 | 9/1993 | (JP) . | |
| 5-69104 | * | 9/1993 | (JP) | A41B/9/00 |
| 406256174A | * | 6/1994 | (JP) | A61K/9/70 |
| 407299152A | * | 11/1995 | (JP) | A61N/2/08 |

OTHER PUBLICATIONS

English translation of Japan Patent Publication 5–69104, Sep. 1993.*

English translation of Japan Patent Publication 5–70553, Sep. 1993.*

English translation of Japan Patent Publication 6–256174, Sep. 1994.*

* cited by examiner

*Primary Examiner*—John P. Lacyk
*Assistant Examiner*—Joseph A. Cadugan
(74) *Attorney, Agent, or Firm*—Armstrong, Westerman, Hattori, McLeland & Naughton LLP

(57) ABSTRACT

There are provided weak magnetic warmth-keeping accessories, anti-hypnotic accessories, health and sanitation articles (excellent in anti-biotic property and anti-mold property) and those having cell-reproducing ability, each having weak magnetism of 2 to 20 gauss.

13 Claims, 8 Drawing Sheets

MEDICAL FABRIC GOODS

This application is a continuation application of Ser. No. 08/605,786 filed Feb. 22, 1996, now abandoned.

BACKGROUND OF THE INVENTION

1. Field of the Invention The present invention relates to medical fabric goods made by utilizing weak magnetism of 2 to 20 gauss, especially to warmth-keeping accessories and health and sanitation articles.

2. Description of Prior Art

A Human being is clad with clothes so as to keep temperature adapted to the environment. For example, in the cold season of winter, a human being is clad with multiple layers of clothes to keep the body temperature to an appropriate degree in order not to catch cold. Moreover, in addition to such clothes, a human being supplementarily puts on accessories such as gloves, mufflers, and the like, to keep warmth effectively of the respective parts of the body.

The conventional accessories are made by utilizing the natural fibers such as wool, hemp, cotton, etc. or the chemical fibers such as nylon, polyester, etc. Those fibers are to maintain the body temperature by preventing the heat from going outside. Those accessories are only to utilize mainly the warmth-keeping effect of air layers of the clothes and the like knitted by fibers. Loss of heat from body has been prevented by the air layers. There has been no conventional product of warmth-keeping accessories having anti-mold properties and anti-biotic properties.

SUMMARY OF THE INVENTION

The main object of the present invention is to provide medical fabric goods such as warmth-keeping fabric goods, fabric goods having anti-biotic properties or anti-mold properties, and health and sanitation fabric goods.

The present invention relates to weak magnetic warmth-keeping accessories, anti-hypnotic accessories, health and sanitation articles and those having cell reproducing capacity, each having weak magnetism of 2 to 20 gauss.

BRIEF DESCRIPTION OF THE DRAWINGS:

FIG. 4A to FIG. 4E are diagrams showing the change in the temperature distribution of the thermography which shows the change in time of the surface temperature of the human body in the case where the conventional corset is put on.

DETAILED DESCRIPTION OF THE INVENTION

Figures 1A, 1B, 1C, 1D, 1E:
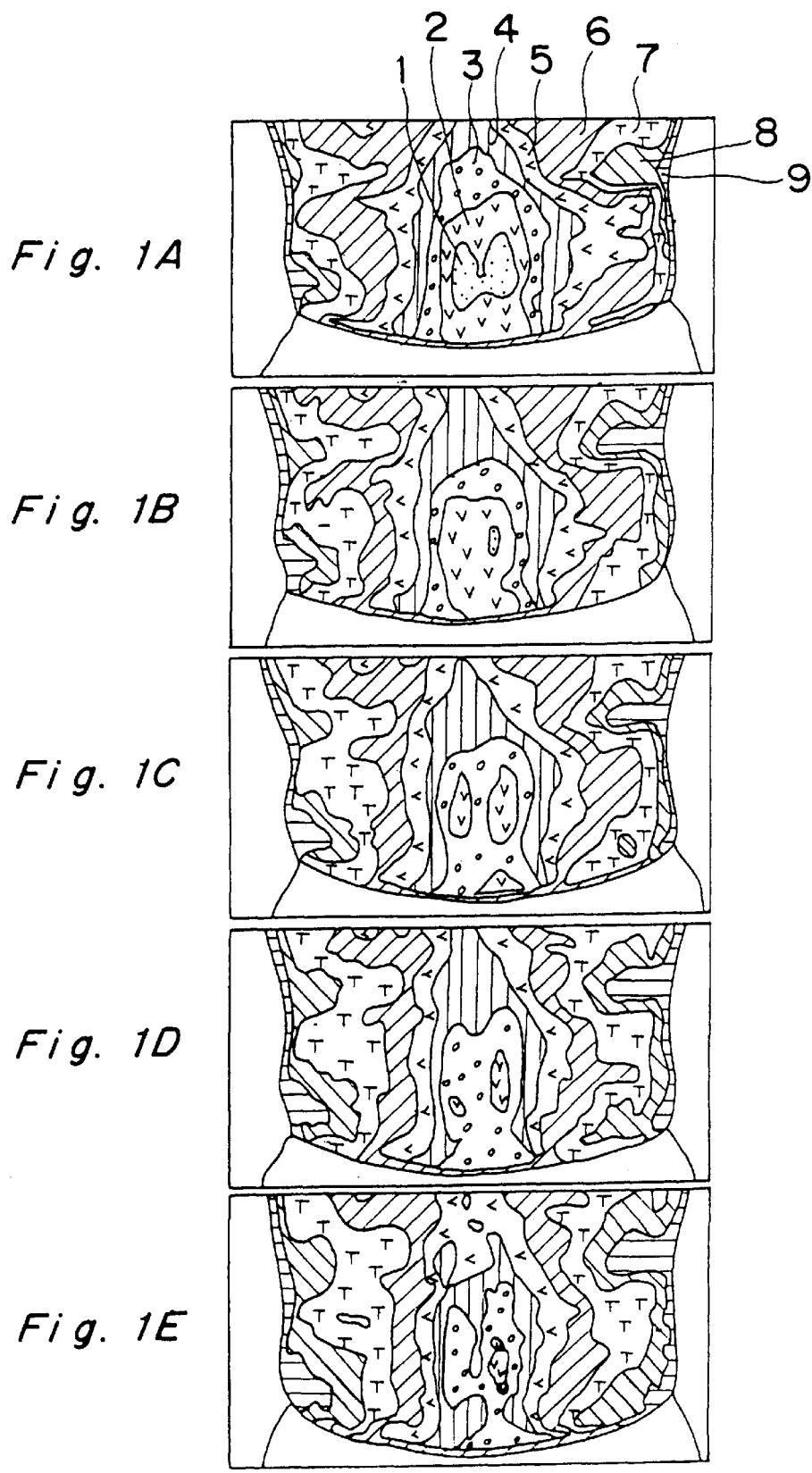
FIG. 1A to FIG. 1E are diagrams showing the change in the temperature distribution of the thermography which shows the change in time of the surface temperature of the human body when the magnetic coating non-woven cloth (8–10 gauss) is used.
Figures 2A, 2B, 2C, 2D, 2E:
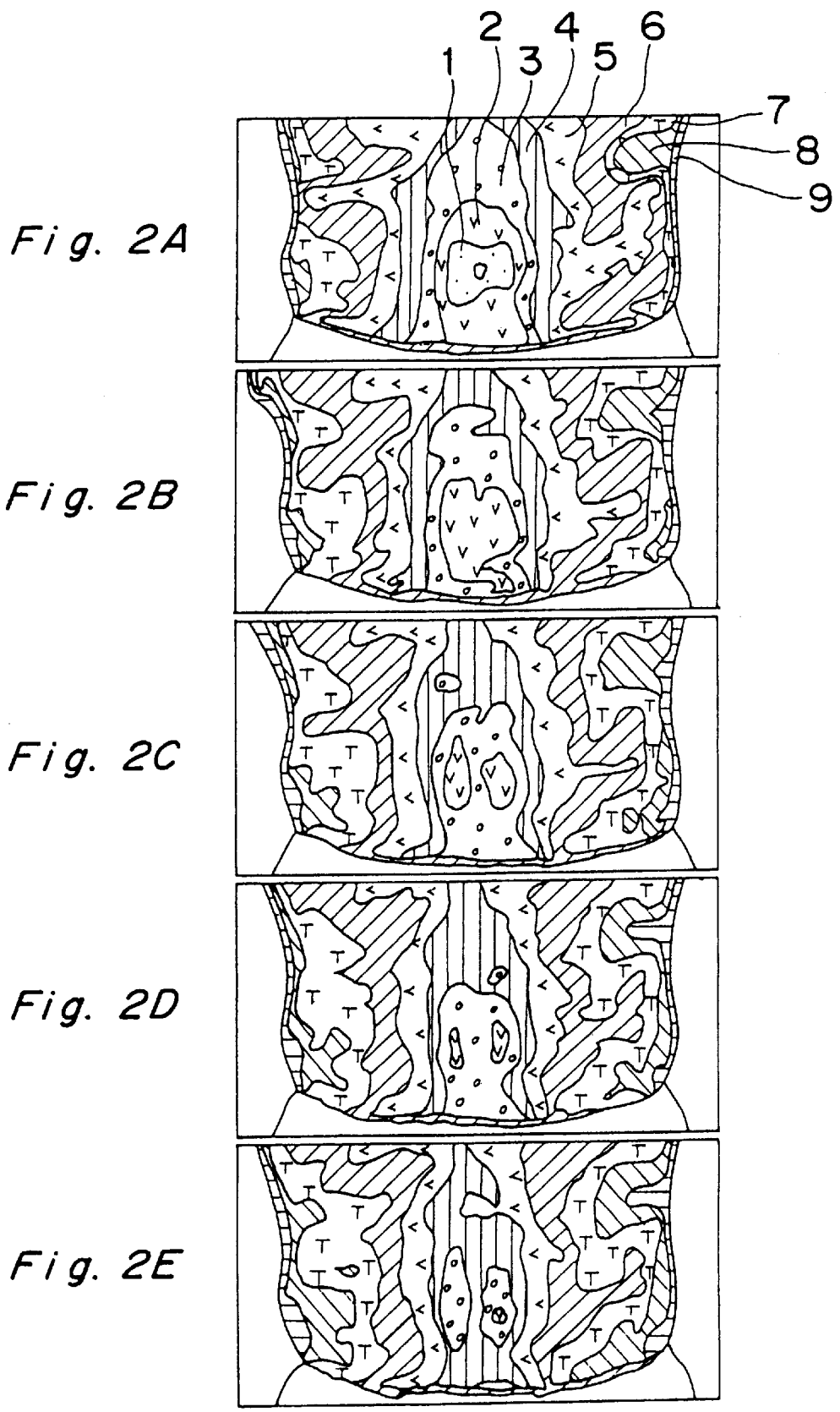
FIG. 2A to FIG. 2E are diagrams showing the change in the temperature distribution of the thermography which shows the change in time of the surface temperature of the human body when the magnetic fiber fabric (8–10 gauss) is used.
Figure 3A:
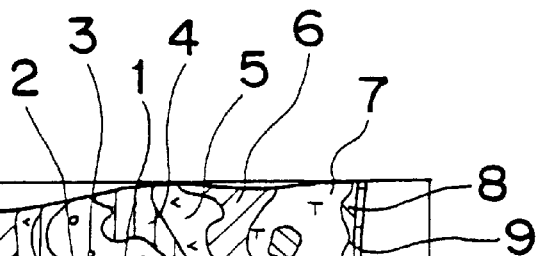
FIG. 3A to FIG. 3E are diagrams showing the change in the temperature distribution of the thermography which shows the change in time of the surface temperature of the human body when the magnet (1,000 gauss) is used.
Figure 3A:
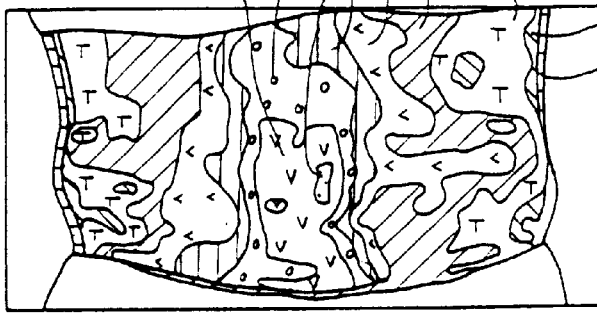
Figure 3B:
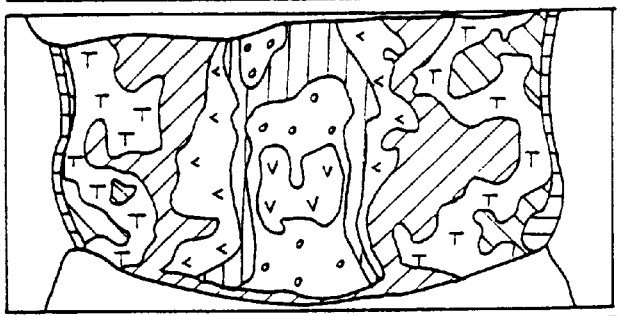
Figure 3C:
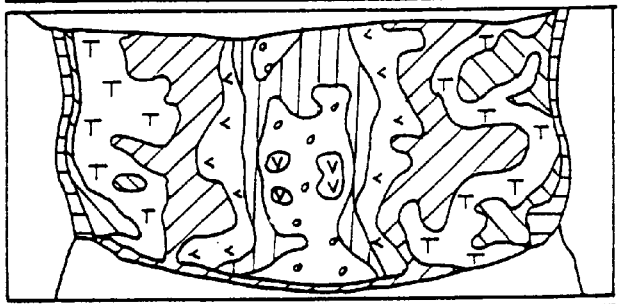
Figure 3D:
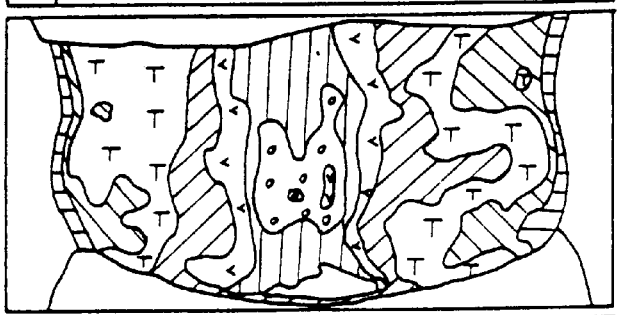
Figure 3E:
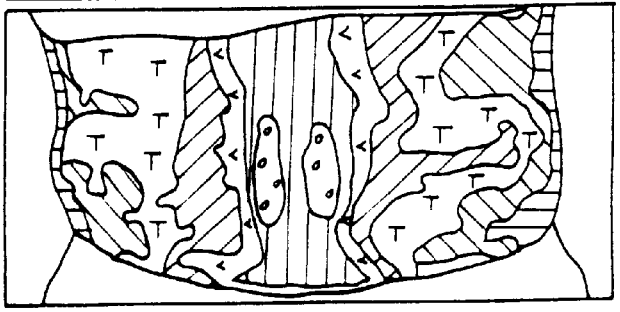
Figure 4A:
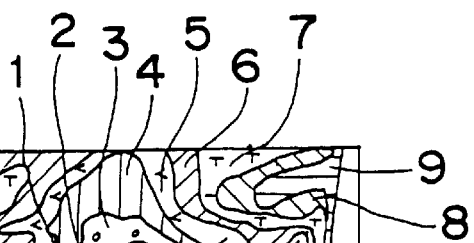
Figure 4B:
Figure 4C:
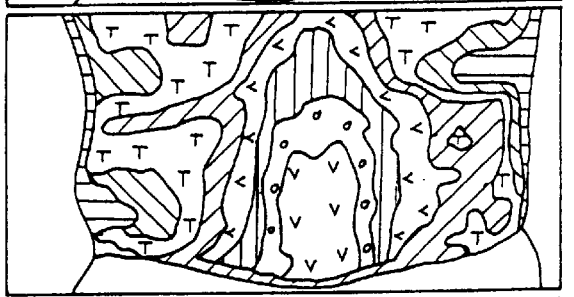
Figure 4D:
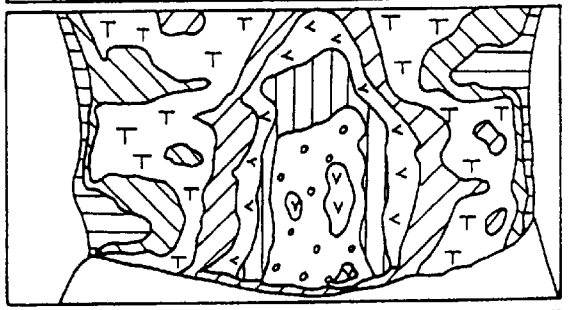
Figure 4E:
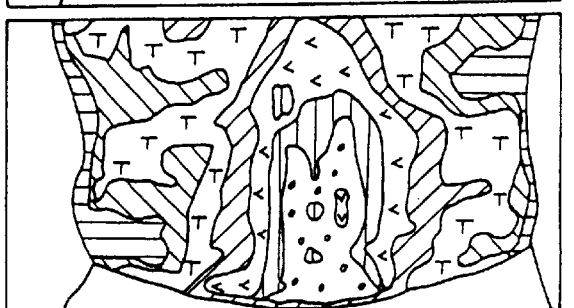

The present invention provides a medical fabric good having a weak magnetism of 2 to 20 gauss.

The medical fabric goods of the present invention means fabric goods applicable to medical use such as warmth keeping, anti-biotic application, inhibition of growth of fungi, anti-molding, anti-hypnotic application, cell reproduction and the like.

Examples of the fabric goods according to the present invention includes gloves, socks, hats, waist pads, pads for arm and leg joints, shoulder pads, belts shoes, insoles for shoes, clothes, wears, sheets, bandages, towels, rugs and the like, made of fabric such as textile, knitted goods, non-woven, film, leather and the like.

The warmth keeping action and the anti-hypnotic action by the medical fabric goods having a weak magnetic property of the present invention may be caused by the improvement of blood circulation.

One of the applications of the medical goods of the present invention is of a warmth keeping accessory.

By subjecting a site or the whole of the human body whose warmth-keeping necessity has occurred to weak magnetic atmosphere of 2 to 20 gauss, temperature of the body can be efficiently maintained.

The magnetism to be applied to the spot where the warmth-keeping is necessary is 2 to 20 gauss, preferably 5 to 15 gauss, more preferably 7 to 11 gauss. Such weak magnetism has so far been recognized as the magnetic intensity of a range which gives no effect to human body. Especially, the magnetism of less than 10 gauss is a value that is adopted as a standard for the magnetic leakage of the linear motor car in Japan, being the weak magnetism to such a degree as is recognized as the magnetic intensity having few adverse effects to the human body. The present inventors have found out that the weak magnetism so recognized has an effect to maintain the temperature. However, if the magnetic level is too small at about 1 gauss, then the effect to keep the temperature is not sufficient. It is therefore preferred to apply magnetism of 2 gauss or more.

The magnetism may be applied in any method of various modes such as to have a fiber contain magnetic material, or to have the fiber surface retain the magnetic material, or to have the magnetic material entangle the net structure of the fiber. And, by cutting these materials into the desired size and shape and sewing the pieces together, optional warmth-keeping accessories may be produced.

Alternatively, it is possible to utilize the conventional products finished as warmth-keeping accessories and give weak magnetism to them to a degree not to inhibit their functions by applying the above mentioned magnetic fiber or magnetic material with, for example, a tape or the like, and make them into the warmth-keeping accessories of the present invention.

In the present invention, the warmth-keeping accessories include gloves, socks, hats, waist pads, pads for arm and leg joints, shoulder pads, belts, shoes, insoles for shoes, and the like. Especially, socks and gloves are useful in the present invention.

The second application of the medical goods of the present invention is of an application of anti-biotic properties to the bacterium species which are often taken as causes for the infectious diseases of the skin and the respiratory organs.

Especially, they have effects against the methicillin-resistant *Staphylococcus aureus, Staphylococcus aureus, E. coli,* and *Pseudomonas aeruginosa.* The warmth-keeping accessories according to the present invention have functions to inhibit the growth of these fungi.

For this reason, the medical fabric goods of the present invention are effectively usable with ease without causing a steamy state by maturation as in the conventional case where a wrist band or a supporter is used, when, for example, a sport player has some disorders of scratches or cuts in a part of the body such as hand, wrist, foot, toe, knee, waist, etc. which should not be cooled.

Furthermore, it is very effective especially for the bed-ridden elderly patient to utilize a blanket, quilt cover, and pajamas produced by using the materials, such as to have the magnetic material contained inside the fibers, for medical fabric goods having anti-fungal properties according to the present invention for therapeutic use.

While studying anti-biotic properties, it has been found that the weak magnetism of 2 to 20 gauss has anti-biotic and anti-mold effects on bacterium species (fungi) causing so-called athlete's foot or dermatophytosis. In particular, the medical fabric goods are effective against incurable dermatophytosis not usually recovered with conventional medicine for dermatophytosis. The dermatophytosis of a patient suffering from diabetes can not be recovered with any kind of conventional medicine for dermatophytosis (anti-fungal agent). However, the present invention is effective against dermatophytosis of a patient suffering seriously from diabetes and incurable dermatophytosis caused by filamentous fungi resistant against any kind of ant-fungal agents, such dermatophytosis being infected widely from sole to ankle and incurable. Now, the present invention is to provide medical fabric goods for therapy of dermatophytosis and health and below-described sanitation accessories for therapy of dermatophytosis.

Moreover, it has been found out that, when the medical fabric goods of the present invention are used as the products to be applied to the head part, e.g. head band, cap, etc. the said accessories show anti-hypnotic effect.

By using the medical fabric goods of the present invention as anti-hypnotic accessories by an ordinary utilizing method, the user is prevented from becoming drowsy. The effect of use is manifested in 10 minutes, i.e., prompt effect is shown. Accordingly, these accessories are very effective for the drivers of passenger cars or trucks.

The medical fabric goods of the present invention show anti-biotic properties against the species of the bacteria which cause the infectious diseases of skin and respiratory organs. Therefore, it is possible to keep the fabric goods placed on the head clean and to provide the head accessories having excellent sanitary effect.

The material lying in the previous stage for producing the medical fabric goods according to the present invention can be molded to produce health and sanitation articles with which only the anti-biotic function or anti-mold function is intended. For example, the product may be utilized as an implement for protecting a wound, a bandage, a substitute for plaster, dirt remover, towel and rug.

As the present invention the medical fabric goods have anti-biotic property or anti-mold property, they can prevent propagation of the bacteria, and are usable with safety. Also, even during storage, propagation of fungi can be prevented.

When the present invention is applied to health and sanitation articles for a wound, the products of the present invention are useful for applying, not only to the self-curable light wound, but also to the large wound formed by surgical operation. When they are used for direct application to the wound site or in a manner to cover the wound, they are effective for preventing the wound site from suppurating. For such purposes, the products may be used in various sizes and the forms of a bandage, cloth, adhesive cloth, or sheet, depending on the shape of the wound after the operation and the purpose of use. The present invention is now to provide wound-site suppuration-preventing articles having a weak magnetism of 2 to 20 gauss. In the present invention, such an article is to be used in the concept covered by the health and sanitation articles.

As described above, the above effects obtainable by the present invention do not exceed the scope of the invention, either when they are optionally combined and made into the object of the product or independently made the object of the product.

More surprisingly, it has been found that the application of weak magnetism of 2 to 20 gauss to, for example, the suppuration site caused by the above species of bacteria such as methicillin-resistant *Staphylococcus aureus,* in a medically pertinent manner in the form of the pad or the like, is extremely effective for obtaining recovery of the suppuration. This is indicative that the weak magnetism of 2 to 20 gauss has a cell reproducing effect. Here, the present invention provides health and sanitation articles utilizing the cell reproducing effect of the weak magnetism of 2 to 20 gauss.

The magnetic materials to be used in the present invention may be any materials having per se magnetism such as magnetic iron ores, magnetic metals, magnetic resins, and the like. Usually, they are used in the form of magnetic particles. In the present invention, the magnetic particles and materials are all preferably in the range of the above magnetic intensity, but they may partly include the portions having the magnetism larger than 20 gauss or the magnetism smaller than 2 gauss, attributed to the raw materials, manufacturing conditions, or other causes.

Magnetic iron ores denote the iron ores emitting magnetism and existing on the earth since the old time. The magnetic iron ores have different levels of magnetic intensity. In order to weaken the magnetism, the ores are pulverized to reduced sizes.

Magnetic metals are the new magnetized metals including magnet alloys.

Magnetic resins are the materials of synthetic resins such as polyethylene incorporated with powders such as ferrite magnet. They can be used in the same manner as the magnetic iron ores, etc.

Typical examples of the magnetic products of the present invention are magnetized non-woven fabrics, which can be prepared according to following processes.

Figure 8:
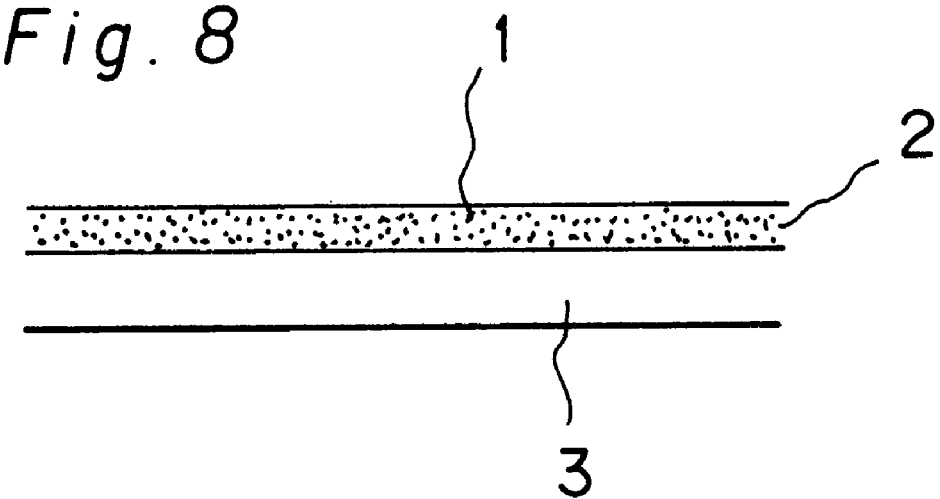
FIG. 8 is the schematic sectional view illustrating the structure of magnetic fabric goods in which a non-woven fabric is laminated on a layer of magnetic ferrite powder dispersed in an binder resin or a synthetic rubber.
Figure 9:
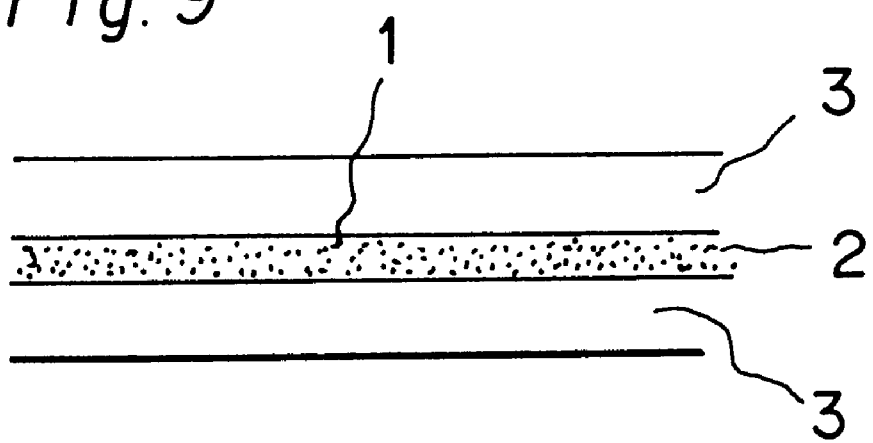
FIG. 9 is the schematic sectional view illustrating the structure of magnetic fabric goods in which a non-woven fabric is laminated on both surfaces of a layer of magnetic ferrite powder dispersed in a binder resin or a synthetic rubber.

1. Ferrite powders (1 in FIGS. 8 or 9) are dispersed into a binder resin or a synthetic rubber, and the obtained dispersion (2 in FIGS. 8 or 9) was coated on the surface of a non-woven fabric (3 in FIGS. 8 or 9). Two or more sheets of the coated non-woven fabric, if necessary, are laminated so that the coated dispersion layer forms an intermediate to give a sandwich sheet.

2. The sandwich sheet is magnetized by the application of voltage in a magnetizing device.

One of the another method of preparing the magnetic fabric is described in Japanese Patent Publication Sho. 61-1525, according to which magnetic powders such as ferrite powders having an diameter of preferably less than 1 µm are mixed with a binder resin which can be spun such as polyamide, polyester, polyvinyl, polyolefine, polyether, and the like under the melting condition of the polymer, and then the mixture is spun according a usual method. This method can be applied to the preparation of fibrous products for woven textile, knitting products and the like in the present invention.

Any other process, of course, can be applied to prepare a magnetized non-woven fabric.

Preferable average diameter of the ferrite powders is about 10 to 400 µm, more preferably 10 to 100 µm.

Examples of the binder resin or synthetic rubber used in the above magnetized non-woven fabric include low density polyethylene, soft polyvinyl chloride, polyvinyl acetate, ethylene vinyl acetate copolymer, polyurethane, polybutadiene rubber, isoprene rubber, neoprene rubber, nitrile butadiene rubber, ethylene propylene rubber and the like. The binder resin or the rubber which has an adhesive property on the non-woven fabric is preferable. The binder resin or the rubber may be used as a dilution or dispersion in a suitable solvent. Of course it may be used in melting state.

The ferrite in the binder resin or synthetic rubber may be preferably used in such a concentration that the surface density of the ferrite is 50 to 250 $g/m^2$ when the dispersion intermediate layer of the sandwich sheet is 0.3 to 3 mm, which is a preferable thickness for a magnetized non-woven fabric of the present invention.

Examples of the non-woven fabric include a natural fiber such as cotton, wool, and the like, a synthetic fiber such as polyethylene, polypropylene, nylon, polyester, acryl, rayon, acetate and the like, which may be a random web, cross web, parallel web, and the like. The thickness of the non-woven fabric is preferably 0.3 to 3 mm.

The voltage for magnetization of the non-woven fabric containing a ferrite layer is dependant on the required magnetic intensity, but in case that the surface density of ferrite is 200 $g/cm^2$, 250 V is applied for 10 gauss and 450 V for 20 gauss, and in case of 100 $g/cm^2$ 300 V for 10 gauss and 450 V for 15 gauss. The magnetized non-woven fabric may have plural non-woven fabric layers of more than two layers.

The following Examples further illustrate the present invention in more detail.

EXAMPLES

In Examples 1 and 2, and Comparative Examples 1 and 2, there were applied to the same person the waist corsets with insertion of the magnetized non-woven fabric (8–10 gauss) prepared by following method, magnetic fiber fabric (8–10 gauss), magnet (1,000 gauss), and non-magnetized fiber fabric, respectively, in the mesh part at the back of the corset, which were taken off after a certain time, and the changes with time of the surface temperatures of the human body were observed on the same person by a thermography (Thermoviewer JTG-4200; manufactured by Nippon Denshi K.K.) to search the warmth-keeping effect as one of the effects of the weak magnetism on the human body.

Preparation of magnetized non-woven fabric:

Ferrite having an average diameter of 40 µm was ground in an ethylene vinyl acetate type binder, and the obtained paste was coated on each one surface of two sheets of cotton non-woven fabric in the amount of 40 $g/m^2$ each, and the coated non-woven fabric were laminated so that the coated layers of the fabrics form the intermediate. The obtained sandwich fabric was dried to give a three layers laminated fabric, which was magnetized by applying a voltage of 450 V for a moment in a magnetizing device, HD-100 (available from Nippon Denji Sokuki K.K.). The magnetism of the obtained magnetized non-woven fabric was 8–10 gauss by a magnetic measure GM-1225.

Example 1

Under the conditions of room temperature of 23° C. and humidity of 65%, a waist corset with insertion at the back mesh part of a magnetized non-woven fabric (8–10 gauss) was applied to the back of the waist over the knit undershirt, over which there were applied a cutter shirt and working clothes. Fifteen minutes later, the corset was taken off, and the surface temperatures of the human body immediately thereafter, 30 seconds later, one minute later, 2 minutes later, and 3 minutes later were measured from the back with a thermography (Thermoviewer JTG-4200; manufactured by Nippon Denshi K.K.) based on the emissivity of 1.

The change with time data of the above results are shown in FIG. 1A to FIG. 1E. In the Figure, the reference number 1 represents the region showing the temperature of 35.5° C. or higher (region 1), the reference number 2 represents the region between 35° C. or higher and less than 35.5° C. (region 2), the reference number 3 represents the region between 34.5° C. or higher and less than 35° C. (region 3), the reference number 4 represents the region between 34° C. or higher and less than 34.5° C. (region 4), the reference number 5 represents the region between 33.5° C. or higher and less than 34° C. (region 5), the reference number 6 represents the region between 33° C. or higher and less than 33.5° C. (region 6), the reference number 7 represents the region between 32.5° C. or higher and less than 33° C. (region 7), the reference number 8 represents the region between 32° C. or higher and less than 32.5° C. (region 8), and the reference number 9 represents the region less than 32° C. (region 9).

The change with time of the thermography is shown in FIGS. 1A–1E. Immediately after taking off the corset (FIG. 1A), the region 1 was shown, and 30 minutes later (FIG. 1B) the region 1 was still observed to remain. One minute later (FIG. 1C), the region 2 became considerably narrower, but the temperature change at the back part was small in comparison with the data of "30 minutes later". In the data of 2 minutes later (FIG. 1D), it was seen that the region 7 came to snap into the region 6 to some extent, but there still remained extensively the regions showing 33.5° C. or higher (regions 2–5). In the data of 3 minutes later (FIG. 1E), there still remained extensively the regions showing 34.5° C. or higher (regions 2, 3). The average temperatures at the back parts in FIG. 1A–FIG. 1E were 34.5, 34.3, 34.1, 33.9 and 33.8° C., in order. The results are shown in Table 1.

Example 2

Except that a magnetic fiber fabric (8–10 gauss) was inserted in the mesh part at the back of the waist corset, measurements by thermography were carried out in the same manner as in Example 1, and the temperature distribution was shown.

The change with time of the thermography is shown in FIG. 2A–FIG. 2E. In the same manner as in Example 1, immediately after taking off the corset (FIG. 2A), the region 1 of relatively wide range was shown, and 30 seconds later (FIG. 2B) the region 1 was observed to disappear, but the regions showing 33.5° C. or higher (regions 2–5) remained extensively. One minute later (FIG. 2C), the region 2 was found to be considerably narrower than after 30 seconds, but the area of the regions showing 33.5° C. or higher (regions 2–5) remained to show scarce change. Further, even 2 minutes later (FIG. 2D), the temperature distribution was found to show scarce change. In the data of 3 minutes later (FIG. 2E), the region 2 still remained. Compared with the data obtained immediately after taking off the corset, the regions showing less than 33° C. (regions 7–9) scarcely spread. The average temperatures at the back parts in FIG. 2A–FIG. 2E were 34.5, 34.3, 34.1, 33.9 and 33.7° C., in order. The results are shown in Table 1.

Comparative Example 1

Except that a magnet (1,000 gauss) was inserted in the mesh part at the back of the waist corset, measurements by thermography were carried out in the same manner as in Example 1, and temperature distribution was shown.

The change with time of the thermography is shown in FIG. 3A–FIG. 3E. In comparison with Examples 1 and 2, immediately after taking off the corset (FIG. 3A), the region 1 existed in relatively narrow range, but 30 seconds later (FIG. 3B] the region 1 disappeared, and the regions showing less than 33° C. (regions 7–9) became wide. One minute later (FIG. 3C), the region 2 became further narrow. Two minutes later (FIG. 3D), the regions showing less than 33° C. (regions 7–9) became wide, and the regions showing 33° C. or higher (regions 2–6) became narrow. Three minutes later (FIG. 3E), the region 2 disappeared. Compared with the data of Examples 1 and 2, the regions showing less than 33° C. (regions 7–9) were widened. The average temperatures at the back parts in FIG. 3A–FIG. 3E were 34.2, 34.0, 33.9, 33.7 and 33.6° C., in order. The results are shown in Table 1.

Comparative Example 2

Except that a non-magnetized fiber fabric was inserted in the mesh part at the back of the waist corset, measurements by thermography were carried out in the same manner as in Example 1, and temperature distribution was shown.

The change with time of the thermography is shown in FIG. 4A–FIG. 4E. In comparison with Examples 1 and 2, immediately after taking off the corset (FIG. 4A), the region 1 existed similarly to Examples 1 and 2, and 30 seconds later (FIG. 4B) the region 1 disappeared. One minute later (FIG. 4C), the region 2 became extremely narrow, and the regions showing less than 33° C. (regions 7–9) became wide. Two minutes later (FIG. 4D), the region 2 almost disappeared, and the regions showing less than 33° C. (regions 7–9) were still wide. Three minutes later (FIG. 4E), the region 3 also became considerably narrow. Compared with the data of Examples 1 and 2, the regions showing less than 33° C. were widened. The average temperatures at the back parts in FIG. 4A–FIG. 4E were 34.4, 34.1, 33.9, 33.7 and 33.6° C., in order. The results are shown in Table 1.

TABLE 1

| Example/Comp. Example | Immediately after | 30 sec. later | 1 min. later | 2 min. later | 3 min. later |
| --- | --- | --- | --- | --- | --- |
| Example 1 | 34.5 | 34.3 | 34.1 | 33.9 | 33.8 |
| Example 2 | 34.5 | 34.3 | 34.1 | 33.9 | 33.7 |
| Comp. Ex. 1 | 34.2 | 34.0 | 33.9 | 33.7 | 33.6 |
| Comp. Ex. 2 | 34.4 | 34.1 | 33.9 | 33.7 | 33.6 |

It has been shown from Examples 1 and 2 and Comparative Examples 1 and 2 that the corset having weak magnetism of 8–10 gauss can be effectively used to keep warmth in comparison with the case of using the non-magnetized corset. Further, as will be observed from the fact that no such warmth-keeping effect was seen when a magnet having magnetism of 1000 gauss was used, it was shown that no warmth-keeping effect was manifested in the case where magnetism was too strong.

In the following Examples 3 to 6, a head band (60 cm×5 cm) was manufactured using a magnetized non-woven fabric of the present invention, it was put on, and the anti-hypnotic effect of said head band was examined. The intensity of the applied magnetism was 8–10 gauss.

Example 3

In around November, 1994, a man of 50 years old, who became sleepy while driving a car, put on a head band made of the above magnetized non-woven fabric, and he gradually felt less sleepy after lapse of 5–6 minutes.

Example 4

In around November, 1994, a man of 61 years old, who became sleepy while driving a car, put on a head band made of a magnetized non-woven fabric of 5 gauss, and he gradually felt less sleepy after lapse of 8–10 minutes.

Example 5

In around November, 1994, a man of 51 years old, who became sleepy while driving a car, put on a head band made of a magnetized non-woven fabric of 15 gauss, and he gradually felt less sleepy after lapse of 5–6 minutes.

Example 6

In around November, 1994, a man of 62 years old, who became sleepy while driving a car, put on a head band of 10 gauss, and he gradually felt less sleepy after lapse of 5–6 minutes.

It was demonstrated by Examples 3 to 6 that the weak magnetic material of the present invention has anti-hypnotic effect.

Example 7

Next, in order to investigate the anti-biotic effect of the weak magnetic products, there were used the methicillin-resistant *Staphylococcus aureus, Staphylococcus aureus, E. coli,* and *Pseudomonas aeruginosa* which are often causative of the infectious diseases of the skin and respiratory organs and a magnetized non-woven fabric (8–10 gauss), to observe the growth of the respective species of bacteria.

There were prepared bacterial liquids with adjustment of the respective bacteria concentrations to about $0.5 \times 10^9$/ml determined by Mcfarland nephelometry, which were respectively inoculated on the BTB agar medium contained in a Petri dish (diameter, 10 cm) (10). A magnetized non-woven fabric (10 gauss) (13) having a size of about 4 cm×about 3 cm was placed on the respective culture medium and cultured at 37° C. for 48 hours to observe whether there exists an area of growth inhibition.

Figure 5A:
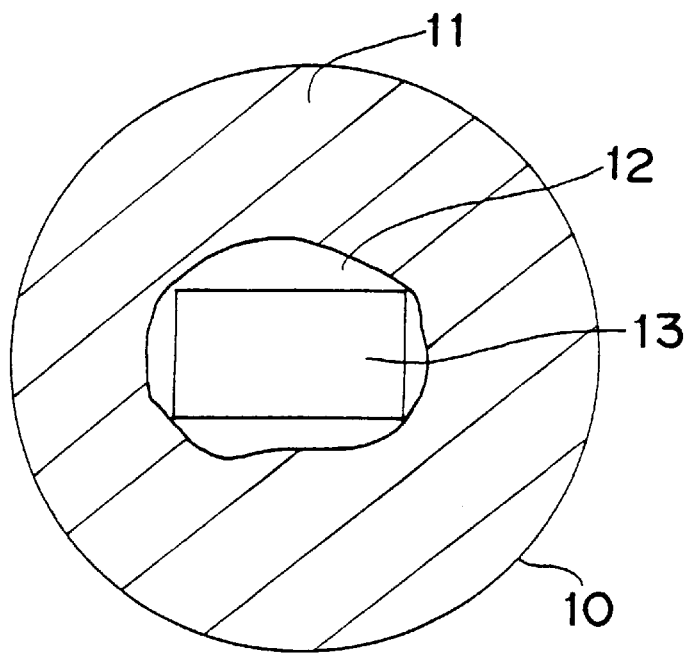
FIG. 5A is a diagram showing schematically the result of observation of anti-biotic effects of the magnetic fabric goods of the present invention to methicillin-resistant Staphylococcus aureus.
Figure 5B:
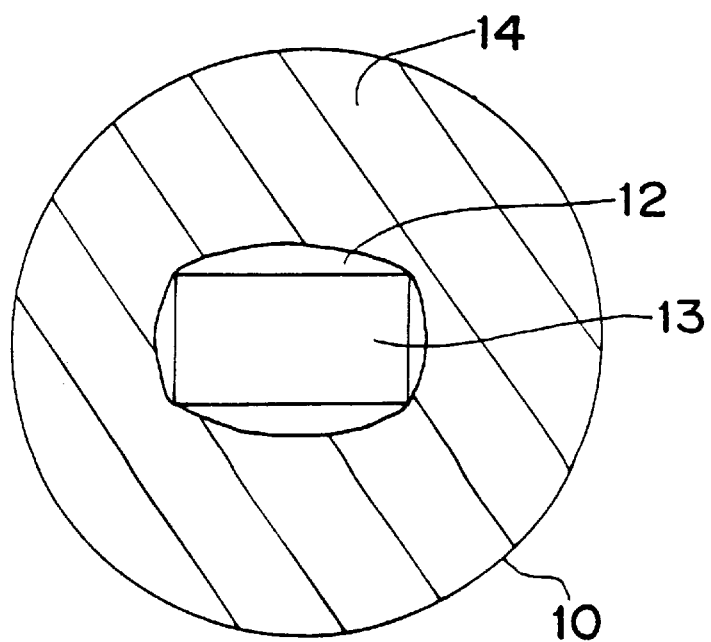
FIG. 5B is a diagram showing schematically the result of observation of anti-biotic effects of the magnetic fabric goods of the present invention to *Staphylococcus aureus*.
Figure 6A:
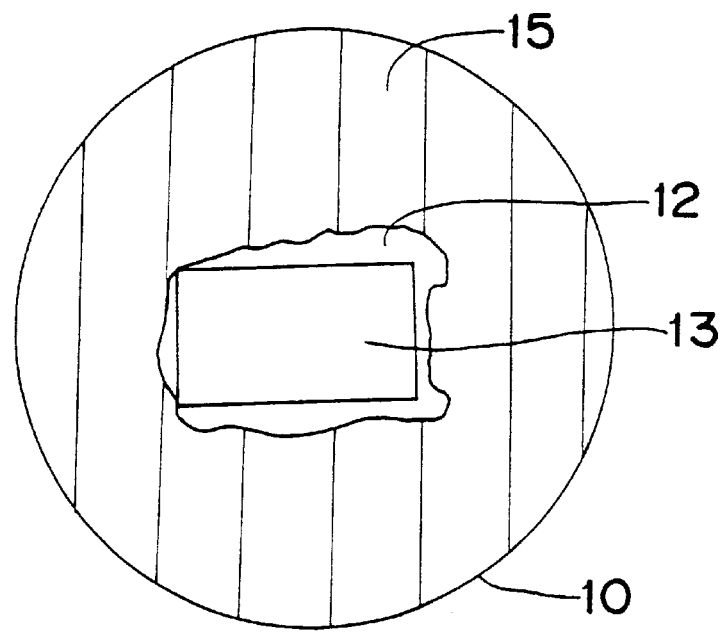
FIG. 6A is a diagram showing schematically the result of observation of anti-biotic effects of the magnetic fabric goods of the present invention to E. coli.
Figure 6B:
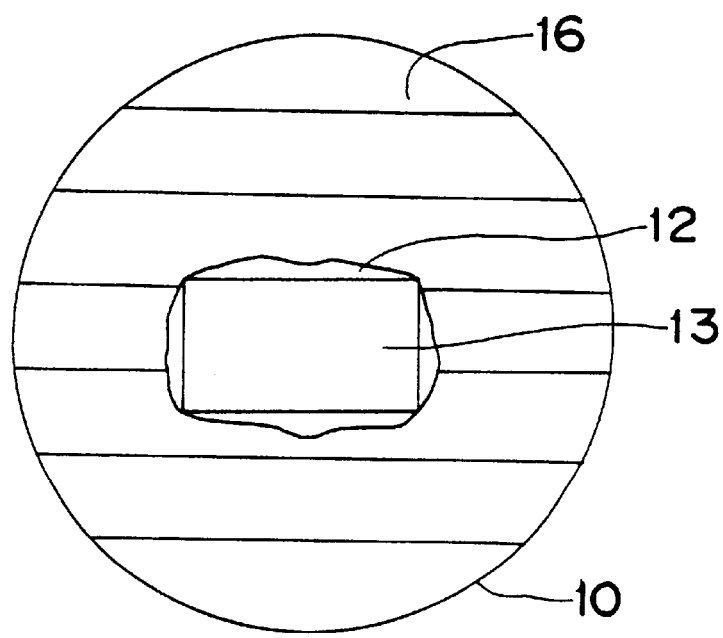
FIG. 6B is a diagram showing schematically the result of observation of anti-biotic effects of the magnetic fabric goods of the present invention to *Pseudomonas aeruginosa*.

As a result, as shown in FIG. 5A and FIG. 5B and FIG. 6A and FIG. 6B, there were observed growth inhibition areas (12) in all Petri dishes (10). FIG. 5A shows the growth inhibition area (12) of methicillin resistant *Staphylococcus aureus*, FIG. 5B that of *Staphylococcus aureus*, FIG. 6C that of *E. coli*, and FIG. 6D that of *Pseudomonas aeruginosa*, respectively. The zones denoted by the reference number 11 (FIG. 5A), 14 (FIG. 5B), 15 (FIG. 6C) and 16 (FIG. 6D) show the growth areas of the respective species of bacteria. Of the four kinds of bacteria, methicillin resistant *Staphylococcus aureus* was most remarkably inhibited to grow by the magnetized non-woven fabric.

Example 8

In this example, investigation was made on the cell regeneration ability of the weak magnetic product.

To a patient suffering from abscess of abdominal wall (after a surgical operation of the sigmoid colon) caused by infectious methicillin resistant *Staphylococcus aureus* (MRSA) having resistance to the administration of the drugs such as vancomycin, habekacin, sulperazone, fosmicin, etc. which are reported to be effective for the infectious disease inducing methicillin resistant *Staphylococcus aureus*, and having an MRSA abdominal wall purulence site of 13 cm×18 cm with the depth of 2 cm, a 0.001 T (10 gauss) magnetized non-woven fabric (8 gauss) of 20 cm×30 cm size was applied. Following the application, the purulence site gradually recovered. It showed full recovery to the original state in 80 days. The large purulence site such as above was fully cured with scarce formation of keloid trace. This fact has led to presume that the magnetic product of the invention possess a cell regeneration effect.

Example 9

Socks made of nylon fiber having magnetism of 0.001 T were put on foot of a patient suffering from widely infected and incurable dermatophytosis caused by filamentous fungi on foot resistant against any kind of ant-fungal agents. The disease caused by filamentous fungi on foot gradually healed and almost completely cured in two weeks.

Example 10

Figure 7:
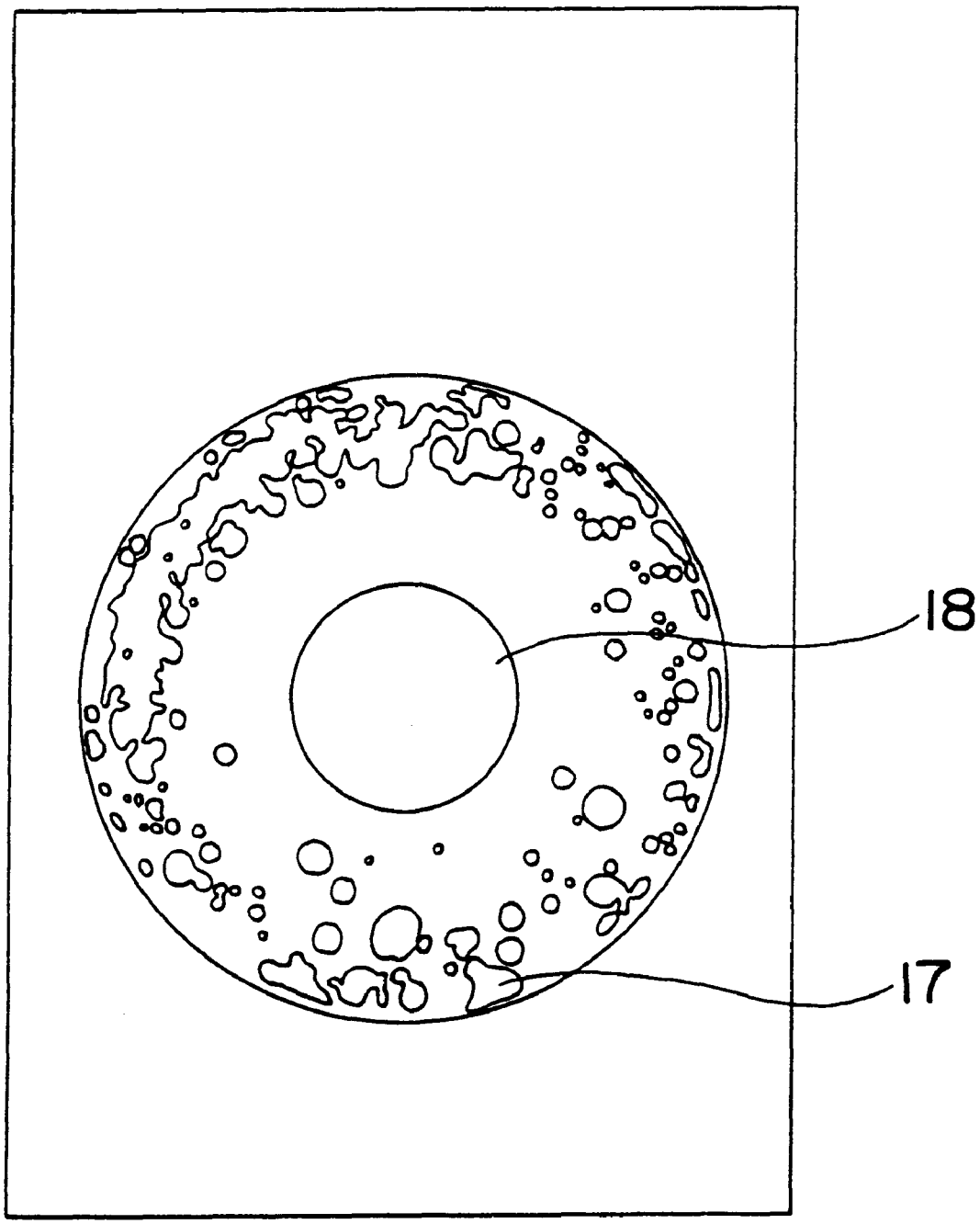
FIG. 7 is a schematic view illustrating the effect of the magnetic fabric goods on the prevention of the growth of dermatophytes.

According to JIS L 1902 dermatophyte dilution was inoculated on a PDA agar medium in Petri dish (diameter: 70 mm), a magnetized non-woven fabric (10 gauss, diameter: 25 mm, thickness: 1 mm) prepared by a similar manner as aforementioned, and incubated at 30° C. for 5 days. The result was schematically illustrated in FIG. 7, in which the dermatophyte colonies (17) were substantially prevented around 9.8 mm peripheral area of the magnetized non-woven fabric (18).

What is claimed is:

1. A method for inhibiting growth of fungi, comprising applying a medical fabric good having a magnetism of 2 to 20 gauss so as to tightly cover a site on an animal where fungi is propagating and so as to extend beyond the site so that the site is isolated from the external environment.

2. A method according to claim 1, in which the fungi are capable of causing a dermatophytosis.

3. A method according to claim 1, in which the fungi are fungi capable of causing athlete's foot or dermatophytosis of patient suffering from diabetes.

4. A method according to claim 1, in which the fabric good having a magnetism of 2 to 20 gauss includes one or more layers of a non-woven fabric laminated on a surface of ferrite powders dispersed in a binder resin or a synthetic rubber.

5. A method according to claim 4, in which the non-woven fabric is a random web, a cross web or a parallel web.

6. A method according to claim 1, in which the fabric good has a magnetism of from 5 to 15 gauss.

7. A method according to claim 1, in which the fabric good has a magnetism of from 7 to 11 gauss.

8. A method for enhancing reproduction of cells in an animal which comprises applying a medical fabric good having a magnetism of 2 to 20 gauss so as to tightly cover a wound site or suppurated site of said animal and so as to extend beyond the site so that the site is isolated from the external environment.

9. A method according to claim 8, in which the fabric good having a magnetism of 2 to 20 gauss includes one or more layers of a non-woven fabric laminated on a surface of ferrite powders dispersed in a binder resin or a synthetic rubber.

10. A method according to claim 9, in which the non-woven fabric is a random web, a cross web or a parallel web.

11. A method according to claim 8, in which the fabric good has a magnetism of from 5 to 15 gauss.

12. A method according to claim 8, in which the fabric good has a magnetism of from 7 to 11 gauss.

13. A method for inhibiting a wound site on an animal from suppurating which comprises applying medical fabric good having a magnetism of 2 to 20 gauss so as to tightly cover the wound site of said animal and so as to extend beyond the site so that the site is isolated from the external environment.

* * * * *